(12) United States Patent
Shemsi et al.

(10) Patent No.: US 12,306,095 B2
(45) Date of Patent: May 20, 2025

(54) SYSTEM AND METHOD FOR DETECTING MERCURY AND TOTAL ORGANIC CARBON IN BURNT PRODUCT

(71) Applicant: KING FAHD UNIVERSITY OF PETROLEUM AND MINERALS, Dhahran (SA)

(72) Inventors: Ahsan Mushir Shemsi, Dhahran (SA); Fahad Mohammed Saleh Al-Ismail, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 339 days.

(21) Appl. No.: 18/155,391

(22) Filed: Jan. 17, 2023

(65) Prior Publication Data

US 2024/0241044 A1 Jul. 18, 2024

(51) Int. Cl.
| | |
|---|---|
| G01N 33/00 | (2006.01) |
| G01N 21/3504 | (2014.01) |
| H05B 3/42 | (2006.01) |

(52) U.S. Cl.
CPC ..... *G01N 21/3504* (2013.01); *G01N 33/0013* (2013.01); *H05B 3/42* (2013.01)

(58) Field of Classification Search
CPC ................ G01N 21/3504; G01N 33/0013
See application file for complete search history.

(56) References Cited

U.S. PATENT DOCUMENTS

2014/0004003 A1* 1/2014 Inoue ................... G01N 31/005
422/83

FOREIGN PATENT DOCUMENTS

| CN | 104769417 B | 4/2019 |
|---|---|---|
| JP | 2010-122160 A | 6/2010 |
| JP | 5365427 B2 | 12/2013 |
| JP | 5617623 B2 | 11/2014 |

* cited by examiner

*Primary Examiner* — Dani Fox
(74) *Attorney, Agent, or Firm* — Oblon, McClelland, Maier & Neustadt, L.L.P.

(57) ABSTRACT

An apparatus, for detecting mercury and total organic carbon, includes a first three-way T connected to a tube furnace, an absorption cell, and a three-way solenoid valve connected to a pressure regulator and a halogen trap. The tube furnace generates burnt products of samples including carbon dioxide, halogen acid, and mercury. The tube furnace is connected to a cylindrical outlet containing a mercury collection tube, which contains an absorptive material comprising gold particles and is disposed in the cylindrical outlet such that gases passing through the cylindrical outlet pass entirely through the mercury collection tube. The pressure regulator regulates a flow speed of an air or oxygen flow fed into the second three-way solenoid valve. The halogen trap removes the halogen acid from the burnt products. The apparatus further includes a non-dispersive infrared detector coupled to the halogen trap and detecting the carbon dioxide in the burnt products.

20 Claims, 4 Drawing Sheets

SYSTEM AND METHOD FOR DETECTING MERCURY AND TOTAL ORGANIC CARBON IN BURNT PRODUCT

BACKGROUND

Technical Field

The present disclosure is directed to total organic carbon (TOC) analysis of samples, and particularly, to a method of detecting mercury and total organic carbon (TOC) simultaneously using a single system.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Emissions from fossil fuel combustion facilities, such as gases of coal-fired utilities and municipal solid waste incinerators, include carbon dioxide and mercury. Excess emission of carbon dioxide and mercury possesses potential environmental hazards. Hence, analysis of environmental solid samples for mercury concentration and total organic carbon (TOC) is critical in environmental impact assessment (EIA) studies. Analysis of TOC and Mercury (Hg) in soil and sediment samples is also conducted for contamination analysis as a part of EIA. Analysis of mercury concentration and TOC is normally done by different instruments. Such instruments are designed based on the direct combustion of samples in the presence of air or oxygen at high temperatures. All carbonaceous components are converted to carbon dioxide which is detected by a non-dispersive infrared (NDIR) detector and expressed as TOC.

Furthermore, mercury released from the combustion of samples is trapped in gold particles and detected by atomic absorption spectrometer (AAS) or atomic fluorescence spectrometer (AFS). Determination of TOC and mercury by two different instruments is a cumbersome, time-consuming, labor-intensive, and an uneconomical process. Moreover, most of the available TOC analyzers are without auto-sampler for solid samples. Hence, there is a need of a system which may overcome the aforementioned limitations.

One object of the present disclosure is to provide a mercury analysis apparatus capable of concurrently conducting TOC analysis.

SUMMARY

The disclosure provides an apparatus for detecting mercury and total organic carbon. The apparatus includes a three-way solenoid valve fluidly connected to a tube furnace, an absorption cell, and to a pressure regulator and a halogen trap. The tube furnace generates burnt products of samples including carbon dioxide, halogen acid, and mercury. The tube furnace is connected to a cylindrical outlet containing a mercury collection tube, which contains an absorptive material comprising gold particles and is sealably disposed in the cylindrical outlet such that gases passing through the cylindrical outlet pass entirely through the mercury collection tube. The pressure regulator regulates a flow speed of an air or oxygen flow fed into the three-way solenoid valve. The halogen trap removes the halogen acid from the burnt products. The apparatus further includes a non-dispersive infrared detector coupled to the halogen trap and detecting the carbon dioxide in the burnt products.

In an embodiment, the mercury collection tube contains gold particles and is in the form of a cylindrical cartridge of uniform outer width having a sealed circumferential surface, a front face, and a back face, wherein the front face and the back face are plugged with quartz wool to retain the absorptive material.

In an embodiment, the pressure regulator controls the flow speed of the air or oxygen flow to be around 25 milliliters per minute (mL/minute).

In an embodiment, the mercury collection tube contains particles of the absorptive material comprising the gold particles uniformly packed in the tube and quartz wool retaining the gold particles from both faces.

In an embodiment, the halogen trap contains calcium oxide and copper wires.

In an embodiment, the outer circumferential surface of the mercury collection tube is a metallic resistive heater configured to heat the absorptive material and release mercury absorbed on the absorptive material.

In an embodiment, an outflow of the carbon dioxide from the NDIR detector is introduced to an exhaust gas line.

In an embodiment, an organic compound is burned at different temperatures to obtain total organic carbon or total carbon including both organic and inorganic carbon.

In an embodiment, the apparatus further includes a first resistive heater surrounding at least a portion of the tube furnace. The first resistive heater heats the samples to form the burnt products at a temperature of 600° C. to 900° C. The second metallic resistive heater heats the mercury collection tube to a temperature (60° C.) to release the mercury to be detected by Atomic absorption or Atomic fluorescence techniques.

The disclosure provides a method of detecting mercury and total organic carbon using a single system. The single system includes a tube furnace, a mercury trap, a mercury detector coupled to the gold trap through a T, a three-way solenoid valve, a pressure regulator coupled to the gold trap, and a halogen trap through a three way solenoid valve, a halogen trap, a NDIR detector coupled to the halogen trap. The three-way solenoid valve is fluidly coupled to the pressure regulator and the halogen trap. The method includes generating, by the tube furnace of the single system, burnt products of samples. The burnt products include carbon dioxide, halogen acid, and mercury. The method further includes regulating, by the pressure regulator of the single system, a flow speed of an air or oxygen flow that is fed into the three-way solenoid valve. The method further includes removing, by the halogen trap of the single system, the halogen acid from the burnt products. The method further includes detecting, by the NDIR detector of the single system, the carbon dioxide included in the burnt products. The tube furnace is connected to a cylindrical outlet containing a mercury collection tube. The mercury collection tube contains an absorptive material comprising gold particles, and is sealably disposed in the cylindrical outlet such that gases passing through the cylindrical outlet pass entirely through the mercury collection tube.

In an embodiment, the mercury collection tube contains gold particles and is in the form of a cylindrical cartridge of uniform outer width having a sealed circumferential surface, a front face, and a back face, wherein the front face and the back face having quartz wool to retain particle and to retain the absorptive material.

In an embodiment, the pressure regulator controls the flow speed of the air or oxygen flow to be around 25 mL/minute.

In an embodiment, the mercury collection tube contains particles of the absorptive material comprising the gold particles uniformly packed and retained there by quartz wool on both sides of the tube.

In an embodiment, the halogen trap contains copper wires.

In an embodiment, the outer circumferential surface of the mercury collection tube is a metallic resistive heater configured to heat the absorptive material and release mercury absorbed on the absorptive material.

In an embodiment, an outflow of the carbon dioxide from the NDIR detector is introduced to an exhaust gas line.

In an embodiment, the method further includes burning an organic compound at different temperatures to obtain total organic carbon and total carbon including both organic and inorganic carbon.

In an embodiment, the single system further includes a first resistive heater surrounding the tube furnace and configured to heat the samples to form the burnt products at a temperature of 600° C. to 900° C. The metallic resistive heater heats the mercury collection tube to a temperature to release Hg to be detected by the Hg detector.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
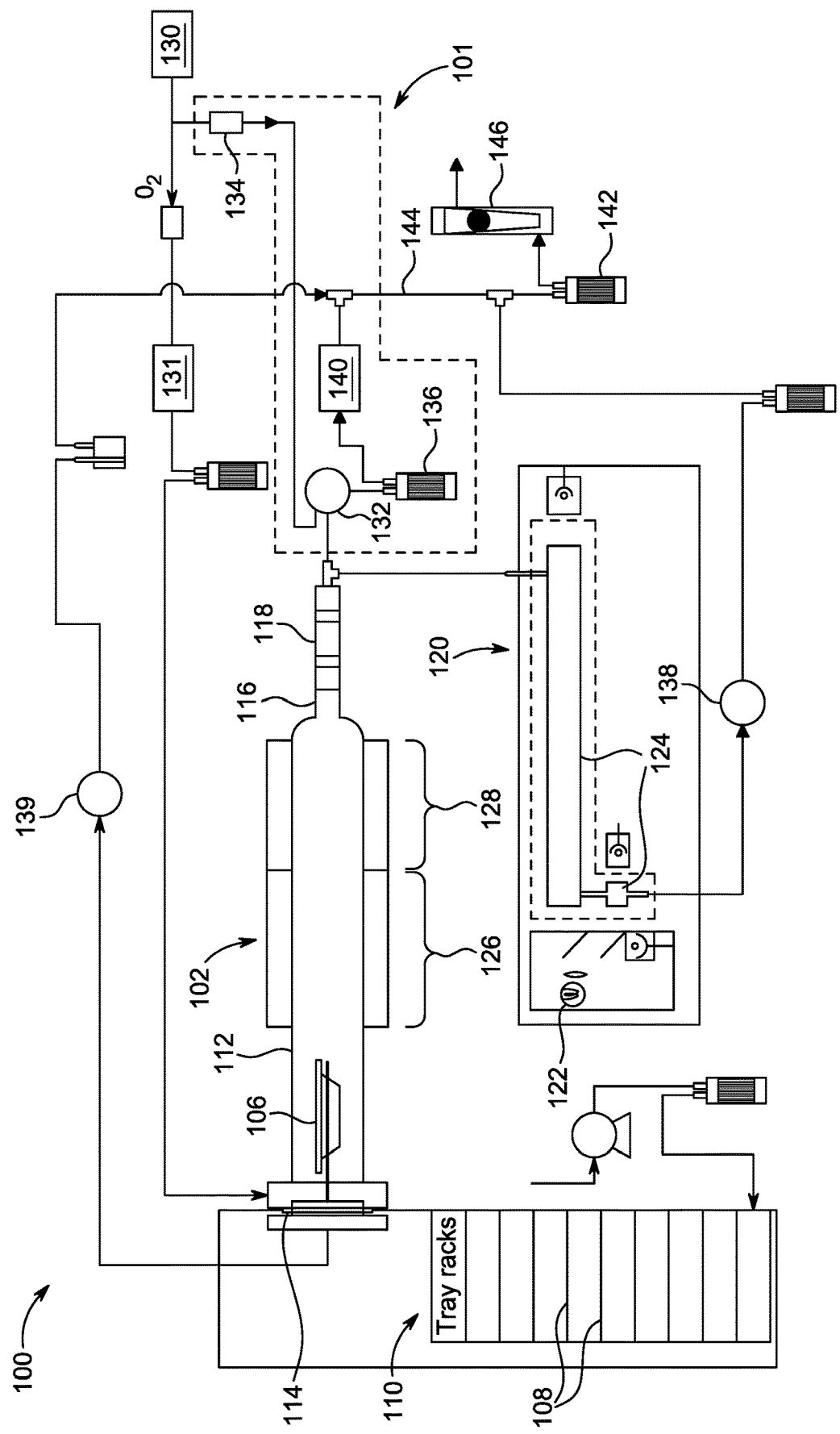
FIG. 1 is a schematic block diagram of a single system for detecting mercury and total organic carbon (TOC), according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present disclosure are directed toward a system and a method for detecting mercury and total organic carbon (TOC). As used herein, the term 'total organic carbon' refers to the amount of carbon found in an organic compound. The system includes a mercury analyzer configured with a carbon dioxide ($CO_2$) non-dispersive infrared (NDIR) detector to determine the mercury and the TOC in a burnt product. Coupling the NDIR detector to the automated mercury analyzer brings two simultaneous analyses together, reduces the manufacturing capital and running cost of the system, and increases the throughput of the analyses due to the automated mercury analyzer.

FIG. 1 illustrates a schematic block diagram of a single system 100 for detecting mercury and TOC in a burnt product. The single system 100 is configured to monitor total mercury and TOC within a burnt product of a sample, which is selected from one or more of a liquid sample, a collected gaseous sample such as an effluent gas from a coal-fired power plant in an inert sampler, and a solid sample. The sample can include, but is not limited to, sediment, soil, food, biological tissue, blood, urine, ore, coal, plastics, crude oil, and wastewater. According to the present disclosure, the sample can be an organic compound such as glucose. In an embodiment, the organic compound can include, but is not limited to, lactose, sucrose, raffinose starch, amylopectin, glycogen, and cellulose.

The single system 100 includes a tube furnace 102 configured to receive the sample in a boat 106 placed in a plurality of trays 108 contained by a tray rack 110. The boat 106 and the plurality of trays 108 can be made of similar or different materials selected from the group consisting of ceramic, glass, quartz, and nickel. The boat 106 can have a boat capacity of 200 milligrams (mg) or 200 microliters (μL). Further, a housing 112 of the tube furnace 102 may include a pyrolyzer formed from an alumina, quartz or glass material (e.g., high temperature quartz) into a cylindrical shape. An inlet 114 of housing 112 is connected to the tray rack 110 and receives the boat 106 from tray rack 110 as the sample is put into the boat 106 and placed in a tray 108. An outlet 116 of the housing 112 is connected to a mercury collection tube 118 and then to an atomic absorption spectrometer (AAS) 120. The AAS 120 includes a light source 122, one or more absorption cells 124, and detectors.

Preferably the housing 112 is horizontally oriented and has a total length that is at least 1.5 times the total length of the outlet 116. Both the housing 112 and the outlet 116 are preferably cylinders of substantially constant inner and outer diameter through a majority of their respective lengths (preferably constant diameter over at least 95% of the total length of the housing and the outlet, respectively). A funnel portion may connect the downstream end of the housing to an upstream end of the outlet such that the housing and the outlet, each having a different outer dimension, may be connected. The housing preferably has an outer dimension that is at least 1.5, preferably 2.5 or three times the outer dimension of the outlet. The total length of the outlet and the collection tube 118 is preferably more than 0.20 times the total length of the housing but less than the total length of the housing. The housing and the outlet are preferably coaxial.

The (mercury) collection tube 118 is configured to couple to or slide into the outlet 116 and maintain a seal such that combustion gases leaving the housing are directed through an opening at a front face of the collection tube thereby permitting ingress of combustion gases and passage through an absorptive material. The absorptive material is effective for removing mercury, e.g., mercury vapor, from the combustion gases leaving the housing and entering the collection tube.

The absorptive material is preferably a gold particles, e.g., as a mixture with a CaO matrix or carrier. In a preferable embodiment, the absorptive material is in particulate form having an average particle diameter of 20-500 µm, preferably 40-400 µm or 100-200 µm. The absorptive material is obtained by mixing gold particles, preferably gold beads of substantially spherical shape to form a bulk material that includes gold particles uniformly dispersed in a carrier. In a preferred embodiment the absorptive material in the collection tube consists of gold particles having a unimodal particle size distribution, e.g., a mean particle size of 5-50 µm, or 20-30 µm or about 25 µm. The bulk absorptive material as a bulk is subsequently comminuted to form particles. The particles of absorptive material may be characterized by exposed gold surfaces on an exterior of a calcium oxide matrix. The gold particles typically have an average particle diameter less than the average particle diameter of the absorptive material and preferably in a range of 5-50 µm. When the gold particles are in the form of wires, the wires preferably have a width of 5-10 µm and a length that is substantially the same as the average particle diameter of the particles of the absorptive material. The presence of exposed gold surfaces on the particles of the absorptive material is observed to provide quick absorption and desorption of mercury. Preferably, at least 25%, more preferably at least 50% of the exterior surface of absorptive material particles is represented by gold surfaces.

Surfaces of the tube furnace 102 that contact the sample can have a coating (e.g., quartz) that minimizes or prevents chemical reactions between the tube furnace 102 and the sample, such as the mercury and carbon dioxide present within the sample. The tube furnace 102 may include a heating and decomposition furnace 126, and a catalyst furnace 128. In an embodiment, a temperature of the tube furnace 102 is set in a range between 650° C. and 800° C. In an embodiment, the temperature of the tube furnace 102 can be set in a range of 680 to 780° C., or 700 to 750° C. The temperature of the heating and decomposition furnace 126 can be increased in stages; first to dry the sample, then to decompose and burn the sample. The tube furnace 102 is configured to generate burnt products of samples in the presence of air or oxygen, which is received from an air/oxygen source 130 via a mass flow controller 131. The mass flow controller 131 can be configured to automatically control a flow rate of a gas according to a preset flow rate value sent as an electric signal, without being affected by use conditions or changes in a gas pressure of the gas. $Hg^{2+}$ and $Hg^+$ ions produced in the heating and decomposition furnace 126 may be sent to the catalyst furnace 128 to get converted into an elemental component, $Hg^0$. The mercury collection tube 118 coupled to the tube furnace 102 is configured to trap the mercury (especially, elemental component, $Hg^0$) included in the burnt products onto gold particles. The trapped mercury is then heated to release the mercury into a carrier gas which transports the mercury into the AAS 120 where the mercury is simultaneously measured in long and short paths. A monochromatic light emitted by the light source 122 at a wavelength of 253.7 nanometers (nm) is attenuated by mercury vapor in the one or more absorption cells 124 according to the Beer-Lambert Law: absorbance is equal to the molar absorptivity times the concentration times the path length.

In an embodiment, the organic compound such as glucose is burned at different temperatures to obtain a total organic carbon and a total carbon including both organic and inorganic carbon. The different temperatures to obtain the total organic carbon and the total carbon including both the organic and inorganic carbon are around 600° C. and 900° C., respectively.

In an embodiment, the tube furnace 102 can be configured to receive a fluid sample from a sample source using a micropipette. For example, the inlet 114 of the tube furnace 102 can be coupled to a tray to collect the fluid sample, or a portion of a fluid or gas (e.g., effluent) flowing through a tray rack, which may or may not be similar to the tray rack 110. The tray rack and an activated charcoal cylinder can remove impurities from the fluid sample prior to the delivery of the fluid sample to the tube furnace 102. The tube furnace 102 can also include a filter that can separate particulate matter (e.g., flue ash) from the fluid sample.

The single system 100 further includes an apparatus 101 configured to detect the carbon dioxide in the burnt product. The apparatus 101 is further configured to be in communication with the mercury collection tube 118 and the tube furnace 102 to detect the carbon dioxide along with the mercury in the burnt product. The apparatus 101 includes a three-way solenoid valve 132 coupled to the tube furnace 102. The three-way solenoid valve 132 is coupled, e.g., fluidly connected, to a pressure regulator 134 and a halogen trap 136 of the apparatus 101. The pressure regulator 134 is configured to regulate a flow speed of an air or oxygen flow that is fed into the three-way solenoid valve 132. In an embodiment, the flow speed of the air or oxygen flow is regulated around 25 milliliter per minute (mL/min).

The tube furnace 102 is configured to generate the burnt products of samples. The burnt products can include carbon dioxide, halogen acid such as hydrofluoric acid (HF), hydrochloric acid (HCl), hydrobromic acid (HBr), and hydroiodic acid (HI), and the mercury. The burnt products can further include hydrogen, nitrogen, sulfur, and carbon monoxide.

The three-way solenoid valve 132 coupled to the tube furnace 102, the pressure regulator 134, and the halogen trap 136 is in association with two-way solenoid valves 138 of the single system 100 used for the analysis of the mercury. Functions of the three-way solenoid valve 132 can be programmed by the AAS 120. The mass flow controller 131 controls the flow of the air or oxygen into the tube furnace 102. The halogen trap 136 is coupled to the three-way solenoid valve 132 in such a way that the burnt products coming out of the mercury collection tube 118 flows to the halogen trap 136 via the three-way solenoid valve 132. The halogen trap 136 is configured to remove the halogen acid and moisture from the burnt products. In an embodiment, the halogen trap 136 contains calcium oxide and copper wires. In an embodiment, the halogen trap 136 can include at least one selected from the group consisting of calcium chloride, calcium sulfate, magnesium perchlorate, zeolites, and silica gel. The apparatus 101 further includes a non-dispersive infrared (NDIR) detector 140 coupled to the halogen trap 136 and is configured to detect the carbon dioxide included in the burnt products. The produced carbon dioxide is delivered to an activated charcoal cylinder 142 via conduits 144 coupled to the NDIR detector 140. Furthermore, an outflow of the carbon dioxide (via an outflow meter 146) from the NDIR detector 140 is introduced to an exhaust gas line such as an exhaust pipe, a flue gas stack, and a propelling nozzle.

Figure 2:
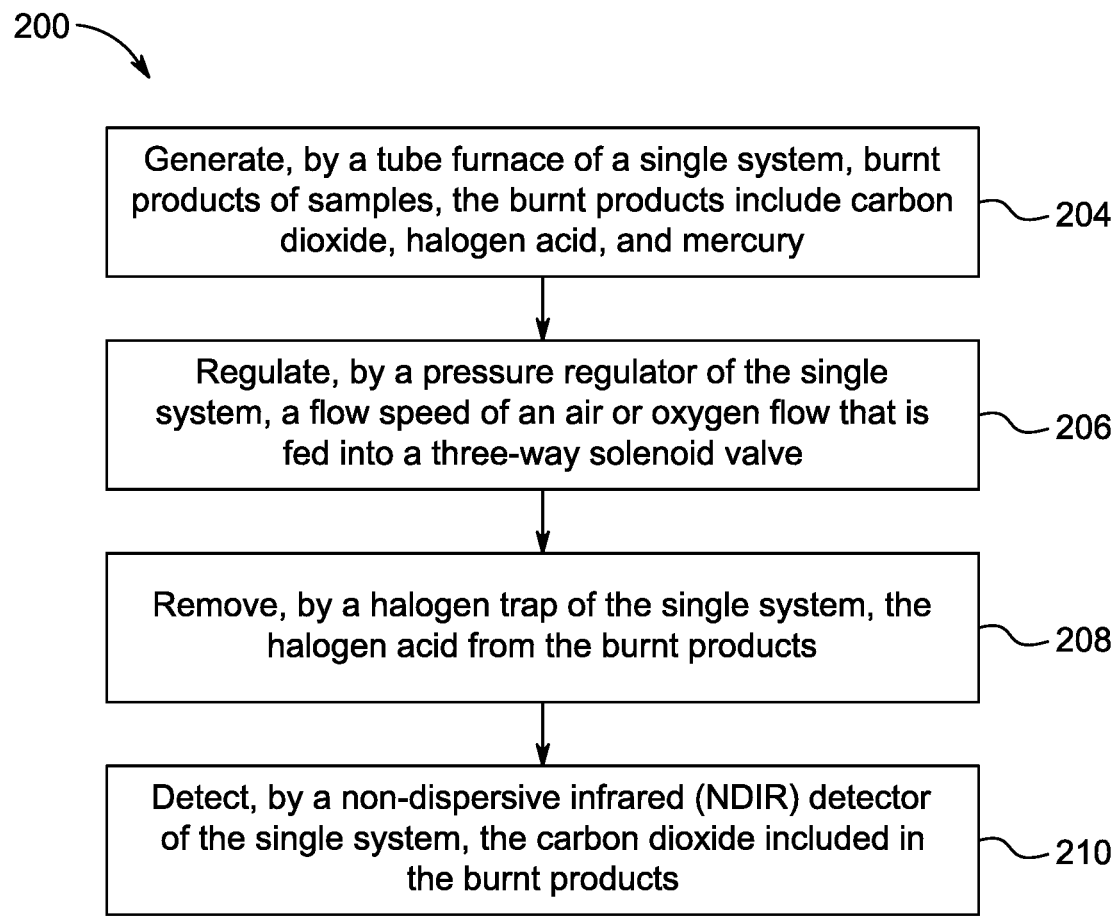
FIG. 2 is a schematic flow chart of a method of detecting the mercury and the TOC, according to certain embodiments.

FIG. 2 illustrates a schematic flow chart of a method 200 to detect the mercury and the TOC using the single system 100. The single system 100 includes the tube furnace 102, the pressure regulator 134, the halogen trap 136, the NDIR detector 140 coupled to the halogen trap 136, and the three-way solenoid valve 132 coupled to the tube furnace 102, the pressure regulator 134, and the halogen trap 136. The order in which the method 200 described is not intended to be construed as a limitation, and any number of the described method steps can be combined in any order to implement the method 200. Additionally, individual steps may be removed or skipped from the method 200 without departing from the spirit and scope of the present disclosure.

At step 202, the method 200 includes generating, by the tube furnace 102 of the single system 100, the burnt products of the samples. The burnt products include the carbon dioxide, the halogen acid, and the mercury. In an embodiment, the temperature of the tube furnace 102 is set in the range between 650° C. and 800° C. In an embodiment, the organic compound is burnt at different temperatures to obtain the total organic carbon and the total carbon including both the organic and inorganic carbon. The total organic carbon is converted to carbon dioxide. In an embodiment, the organic compound is glucose etc. The different temperatures to obtain the total organic carbon and the total carbon including both the organic and inorganic carbon are around 600° C. and 900° C., respectively.

At step 204, the method 200 includes regulating, by the pressure regulator 134 of the single system 100, the flow speed of the air or oxygen flow that is fed into the three-way solenoid valve 132. In an embodiment, the flow speed of the air or oxygen flow is regulated around 25 mL/minute.

At step 206, the method 200 includes trapping, by the mercury collection tube 118 of the single system 100, the mercury included in the burnt products onto gold particles. The mercury collection tube 118 is coupled between the tube furnace 102 and the three-way solenoid valve 132. The obtained carbon dioxide is free of mercury.

At step 208, the method 200 includes removing, by the halogen trap 136 of the single system 100, the halogen acid from the burnt products. In an embodiment, the halogen trap 136 contains the copper wires and calcium oxide.

At step 210, the method 200 includes detecting, by the NDIR detector 140 of the single system 100, the carbon dioxide included in the burnt products. In an embodiment, after the NDIR detector 140 detects carbon dioxide, the data corresponding to the carbon dioxide can be digitally represented in the form of a graph, and can be saved as a comma-separated values (CSV) file. The data can be taken as an area of a peak or a peak height. The integration of the peak area is proportional to the concentration of carbon dioxide. The peak height also corresponds to carbon dioxide concentration at low level. The carbon dioxide is converted to total organic or inorganic carbon. The data can be processed for making calibration graphs and also for sample measurements. The outflow of the carbon dioxide from the NDIR detector 140 is introduced to the exhaust gas line.

Figure 3:
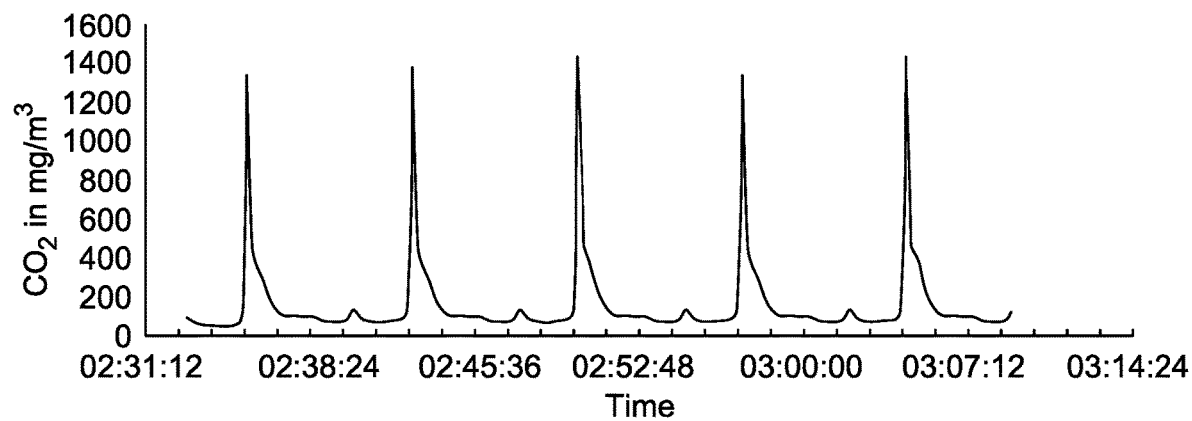
FIG. 3 is a graph depicting results of TOC stability response of the single system, according to certain embodiments.
Figure 4:
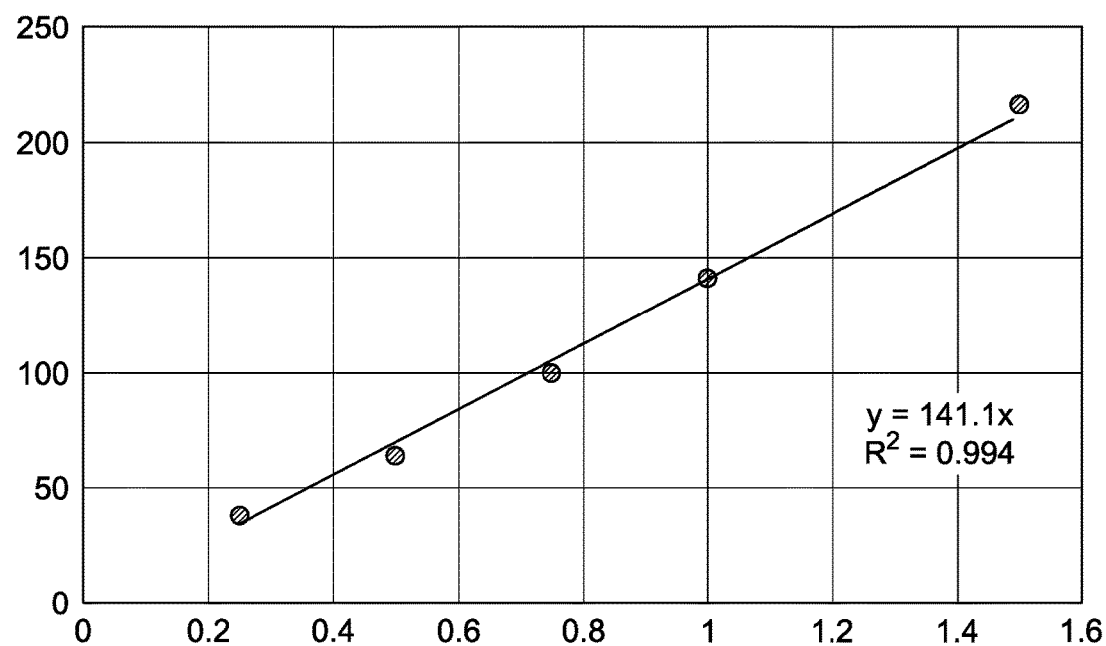
FIG. 4 is a graph depicting calibrations of the single system for TOC at 600° C., according to certain embodiments.
Figure 5:
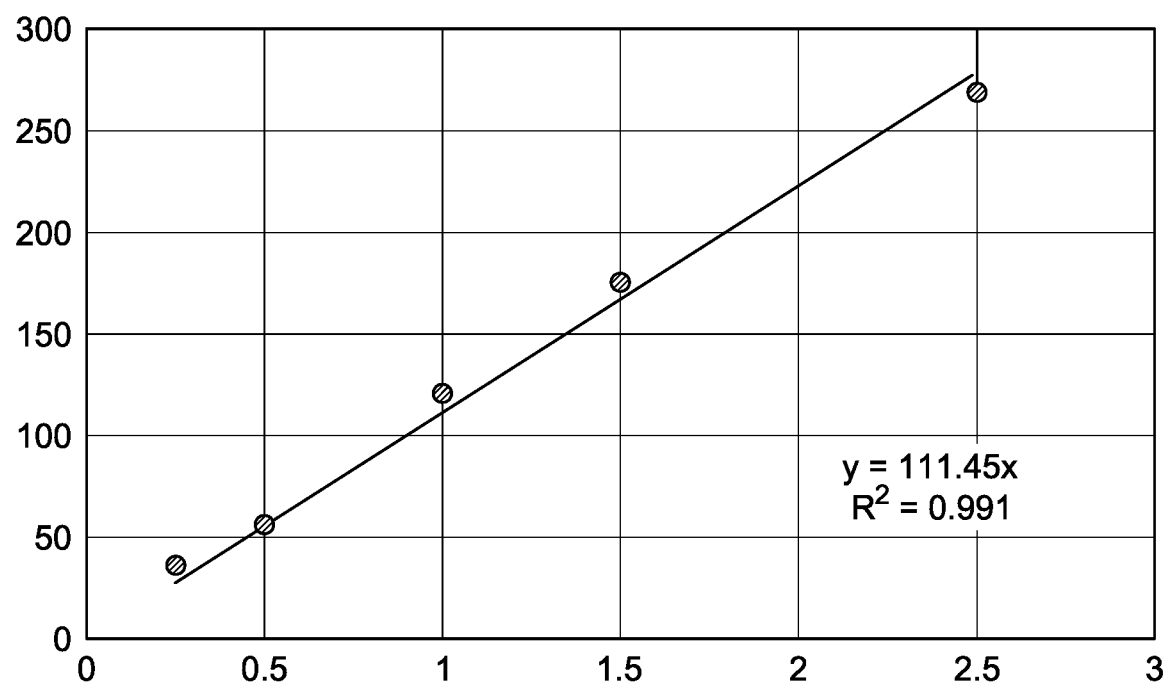
FIG. 5 is a graph depicting calibrations of the single system for total carbon including both organic and inorganic carbon at 900° C., according to certain embodiments.

In an embodiment, the method 200 includes performing a calibration to the single system 100 based on the detection of the carbon dioxide. In an exemplary embodiment, a standard organic compound (glucose or potassium hydrogen phthalate) was burned at different temperatures to differentiate the TOC and the total carbon including both the organic and inorganic carbon. The results of the TOC stability response of the single system 100 is shown in FIG. 3. FIG. 3 shows that the amount of the total organic carbon is almost same with increasing time. The calibration is performed based on the detection of the carbon dioxide. Results of combustion of the TOC and the total carbon including both the organic and inorganic carbon at various temperatures are shown in FIG. 4 and FIG. 5. Regression analysis ($R^2$) values of 0.994 and 0.991 were obtained at 600° C. and 900° C. for the TOC and the total carbon including both the organic and inorganic carbon, respectively, as shown in FIGS. 4-5.

The present disclosure provides a single system 100 capable of determining mercury content and TOC simultaneously. The single system 100 has low operational, maintenance, instrumental, and running costs. The single system 100 may find results for the samples including solid samples, liquid samples, and gas samples. Determination of the TOC and mercury by the single system 100 is a simple, time-saving, labor-superficial, and an economical process. The single system 100 can be used to control or check the mercury and TOC level during processing of various samples such as coal, crude oil, shale oil, sediment, atmospheric air, blood, calcium fluoride, sludge, sulfide, silica, bauxite, and copper ore.

Numerous modifications and variations of the present disclosure are possible in light of the above teachings. It is therefore to be understood that within the scope of the appended claims, the invention may be practiced otherwise than as specifically described herein.

The invention claimed is:

1. An apparatus, comprising:
a three-way solenoid valve fluidly connected to a tube furnace through a mercury collection tube, a non-dispersive infrared (NDIR) detector through a halogen trap, and a gas supply line;
wherein the tube furnace is configured to generate burnt products of samples, the burnt products including carbon dioxide, halogen acid, and mercury;
wherein the tube furnace has a cylindrical outlet containing or connected to the mercury collection tube, wherein the mercury collection tube contains an absorptive material comprising gold particles and is sealably disposed in the cylindrical outlet such that gases passing through the cylindrical outlet pass entirely through the mercury collection tube;
wherein the gas supply line is fluidly connected to a pressure regulator configured to regulate a flow speed of an air or oxygen flow through the three-way solenoid valve, the halogen trap and the NDIR detector;
wherein the halogen trap contains magnesium perchlorate and is configured to remove the halogen acid from the burnt products; and
wherein the NDIR detector is coupled to the halogen trap and configured to detect the carbon dioxide in the burnt products.

2. The apparatus of claim 1, wherein the mercury collection tube contains gold particles and is in the form of a cylindrical cartridge of uniform outer width having a sealed outer circumferential surface, a front face and a back face, wherein the front face and the back face are packed with quartz wool to retain the absorptive material.

3. The apparatus of claim 1, wherein the pressure regulator is configured to control the flow speed of the air or oxygen flow to 20-30 milliliter per minute (mL/minute).

4. The apparatus of claim 1, wherein the gold particles are uniformly dispersed in the absorptive material in the mercury collection tube.

5. The apparatus of claim 1, wherein the halogen trap further contains calcium oxide and copper wires.

6. The apparatus of claim 1, wherein the outer circumferential surface of the mercury collection tube is a metallic resistive heater configured to heat the absorptive material and release mercury absorbed on the absorptive material.

7. The apparatus of claim 1, wherein the NDIR detector is fluidly connected to an exhaust gas line.

8. The apparatus of claim 1, wherein the tube furnace is configured to burn an organic compound at different temperatures to separately detect total organic carbon (TOC) at a first tube furnace temperature and total carbon including both organic and inorganic carbon at a second tube furnace temperature.

9. The apparatus of claim 1, wherein the three-way solenoid valve is connected to the mercury collection tube through a three way tube junction.

10. The apparatus of claim 6, further comprising:
a first resistive heater surrounding the tube furnace and configured to heat the tube furnace to form the burnt products at a temperature of 600° C. to 900° C.,
wherein the metallic resistive heater is configured to heat the mercury collection tube to a temperature to release mercury.

11. A method of detecting mercury and total organic carbon using a single system, wherein the single system includes a tube furnace, a pressure regulator, a mercury collection tube, a halogen trap, a non-dispersive infrared (NDIR) detector, and a three-way solenoid valve, the method comprising:
generating, by the tube furnace, a burnt product of a sample, the burnt product including carbon dioxide, halogen acid, and mercury all in gaseous form;
regulating, by the pressure regulator, a flow speed of an air or oxygen flow that is fed into the s three-way solenoid valve;
removing, by the halogen trap, the halogen acid from the burnt product; and
detecting, by the NDIR detector, the carbon dioxide in the burnt product,
wherein the tube furnace has a cylindrical outlet containing the mercury collection tube, wherein the mercury collection tube contains an absorptive material comprising gold particles, and is sealably disposed in the cylindrical outlet such that the burnt product passing through the cylindrical outlet pass entirely through the mercury collection tube.

12. The method of claim 11, wherein the mercury collection tube contains gold particles and is in the form of a cylindrical cartridge of uniform outer width having a sealed outer circumferential surface, a front face and a back face, wherein the front face and the back face are a quartz wool mesh material to retain the absorptive material.

13. The method of claim 11, wherein the pressure regulator is configured to control the flow speed of the air or oxygen flow to 20-30 milliliter per minute (mL/minute).

14. The method of claim 11, wherein the absorptive material in the mercury collection tube contains comprises the gold particles uniformly dispersed thereon.

15. The method of claim 11, wherein the halogen trap contains calcium oxide and copper wires.

16. The method of claim 11, wherein the outer circumferential surface of the mercury collection tube is a metallic resistive heater configured to heat the absorptive material and release mercury absorbed on the absorptive material.

17. The method of claim 11, wherein the NDIR detector is fluidly connected to an exhaust gas line.

18. The method of claim 11, further comprising:
burning an organic compound at different temperatures to obtain a total organic carbon at a first temperature and a total carbon including both organic and inorganic carbon at a second temperature.

19. The method of claim 11, wherein the three-way solenoid valve is connected to the mercury collection tube through a three way tube junction.

20. The method of claim 16, wherein the single system further includes
a first resistive heater surrounding the tube furnace and configured to heat the tube furnace to form the burnt products at a temperature of 600° C. to 900° C.,
wherein the metallic resistive heater is configured to heat the mercury collection tube to a temperature to release mercury.

* * * * *